United States Patent [19]

Austad

[11] 4,157,085
[45] Jun. 5, 1979

[54] SURGICALLY IMPLANTABLE TISSUE EXPANDING DEVICE AND THE METHOD OF ITS USE

[75] Inventor: Eric D. Austad, Ann Arbor, Mich.

[73] Assignee: Dow Corning Corporation, Midland, Mich.

[21] Appl. No.: 889,787

[22] Filed: Mar. 24, 1978

[51] Int. Cl.² .................. A61B 19/00; A61F 1/00
[52] U.S. Cl. ........................... 128/1 R; 3/1; 3/36; 128/DIG. 21
[58] Field of Search ............. 3/1, 36; 128/1 R, 334 R, 128/DIG. 21

[56] References Cited

U.S. PATENT DOCUMENTS

| 3,093,831 | 6/1963 | Jordan | 3/1 |
| 3,416,160 | 12/1968 | Arion | 3/36 |

OTHER PUBLICATIONS

Radovan Subcutaneous Tissue Expander-Introductory Data Sheet, Heyer-Schulte Corp., 600 Pine Ave., Goleta, Calif., pp. 1-5, Apr. 1977.

*Primary Examiner*—Ronald L. Frinks
*Attorney, Agent, or Firm*—Max J. Kenemore

[57] ABSTRACT

A surgically implantable device for expanding skin and mucous tissue comprises a partially collapsed sealed envelope formed from a material which is permeable to extracellular body fluid. The envelope contains a material which establishes an osmotic potential across the envelope wall. Body fluid crosses the membrane to fill the envelope. As the envelope fills it expands the adjacent tissue. In use, the partially collapsed envelope is surgically implanted under the tissue to be expanded and is allowed to absorb fluid whereby expansion of the bag and subsequent tissue expansion is accomplished. A variety of surgical procedures using the expanded tissue are possible.

15 Claims, 2 Drawing Figures

SURGICALLY IMPLANTABLE TISSUE EXPANDING DEVICE AND THE METHOD OF ITS USE

BACKGROUND OF THE INVENTION

1. Field of the Invention

This invention relates generally to surgical devices and procedures; and, more specifically, to surgically implantable devices for expanding skin tissue and mucous membrane.

2. Description of the Prior Art

The expansion of skin is an observed phenomenon. Abdominal skin is seen to expand in pregnancy and in progressing obesity.

It is known to take advantage of this phenomenon. One device, developed by C. Radovan causes skin to expand by surgically implanting an inflatable bag under the skin. The bag is connected by a tube to a reservoir which is also implanted. The bag is incrementally inflated by hypodermically injecting a fluid into the reservoir from time to time. Inflation of the bag causes the skin tissue to expand.

Such a device and procedure have important advantages. Skin tissue needed for plastic surgery can be generated adjacent its site of use. The expanded skin is partially loosened and stretched to the area of surgery. Thus, such surgery can be accomplished with skin having color and texture characteristics similar to the repaired area, and the repair is made with a minimum of additional disturbance to the vascular supply of the expanded skin.

The device and procedure of Radovan have certain disadvantages. The requirement for an inflatable bag attached by a tube to a reservoir, all of which are to be surgically implanted, limits such a device to larger projects. For instance, such a device would be impractical for use in expanding tissue for cleft lip or palate repair of an infant.

Incremental inflation of the bag by hypodermic means is an inconvenience to both the patient and the physician, requiring a regular schedule of visits over a period of several weeks. Each subsequent injection of fluid into the reservoir can result in additional discomfort for the patient. Each such subsequent injection can also provide an opportunity for an undesirable infection.

SUMMARY OF THE INVENTION

It is an object of this invention to overcome the disadvantages of the prior art.

It is also an object of this invention to expand skin tissue and mucous membrane.

It is a further object of this invention to expand tissue and membrane for use in subsequent surgical procedures.

It is still another object of this invention to furnish tissue and membrane for reconstructive surgical procedures which is similar in physical characteristics to the tissue and membrane normally present at the location of the procedure.

It is yet another object of this invention to furnish tissue and membrane which has an adequate vascular supply for reconstructive surgical procedures.

It is a further object of this invention to expand tissue and membrane while avoiding the need for incremental hypodermic injections to cause the expansion.

It is also an object of this invention to make possible the expansion of tissue and membrane in relatively small areas. These and other objects are accomplished by a surgically implantable device for expanding skin tissue and mucous membrane which comprises, generally speaking, a partially collapsed, sealed flexible envelope formed from a membrane which is permeable to extracellular body fluid. The envelope contains a material which provides sufficient osmotic potential across the membrane to draw extracellular body fluid across the membrane.

The fluid drawn into the envelope causes it to expand. The expanding envelope causes the tissue beneath which it has been implanted to expand.

Another aspect of the invention includes the method of using the device to expand skin tissue and mucous membrane. The method includes, generally, surgically implanting the device beneath the tissue sought to be expanded and allowing the device to expand, resulting in a corresponding tissue expansion. In most cases the device is removed after the tissue has been expanded. Use of the expanded tissue is subsequent surgical procedures, especially in plastic surgery, is also contemplated by this aspect of the invention.

BRIEF DESCRIPTION OF THE DRAWINGS

The invention is described below in greater detail with reference to the drawings in which.

DETAILED DESCRIPTION

Figure 1:
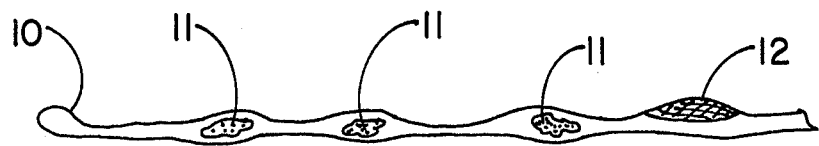
FIG. 1 shows schematically and in cross-section the device of the present invention prior to expansion.

Referring more specifically to FIG. 1, there is shown envelope 10, which is partially collapsed. Envelope 10 contains material 11 which provides an osmotic potential across the walls of envelope 10.

Envelope 10 can be formed from any useful material. Suitable materials are membranes which are permeable to extracellular body fluid under osmotic pressure. Typical of such materials are cellulose acetate, cellulose acetate butyrate, cellulose nitrate, crosslinked polyvinyl alcohol, polyurethanes, nylon 6, nylon 6.6, aromatic nylon, polyvinyl acetate, plasticized polyvinylacetate, polyvinyl butyrate, ethylene vinyl acetate copolymers, polyethylene, polypropylene, polyisobutylene, polyvinyl chloride, plasticized polyvinylchloride, natural rubber, silicone rubber and polybutadiene.

Silicone rubber is a preferred membrane material for envelope 10 because of its relative strength and flexibility at useful membrane thicknesses and because of its well known compatibility by animal tissue. A preferred material is Silastic ® silicone elastomer available from Dow Corning Corporation.

The thickness of the membrane which forms envelope 10 can vary depending on such considerations as the overall size of envelope 10, the desired membrane strength and the desired rate of osmatic flow. The membrane is typically from about 0.001 to about 0.020 inch (0.0254 mm to about 0.5080 mm) thick.

A preferred membrane thickness is from about 0.003 inch (0.0762 mm) to about 0.012 inch (0.3048 mm). Membrane thicknesses in this range are preferred because of the combination of relative strength and relatively rapid expansion of the envelope they provide. It is observed from experimental procedures that the expansion rate of the envelope varies substantially inversely as the membrane thickness. For example, an envelope 10 having a membrane thickness of 0.003 inch (0.0762 mm) containing a certain material 11 in sufficient quantity to result in a constantly saturated solution within an 18 cc envelope, will expand at a rate of about 1.2 cc per day. An envelope 10 containing the same material 11 but having a membrane thickness of 0.006 inch (0.1524 mm) will expand at a rate of 0.6 cc per day.

Envelope 10 can be of any size suited to the individual tissue expansion project for which it is used. For example a relatively small envelope having an expanded volume of about 10 ml. would typically be selected to expand tissue for subsequent repair of a cleft lip or palate in an infant. On the other hand, an envelope capable of expansion to 250 or 300 cc. would more likely be selected to expand skin tissue for subsequent acceptance of a mammary prosthesis.

The shape of the envelope is not critical. It may usefully be adjusted to suit the geometry of a particular tissue expansion project.

Envelope 10 is normally closed with seal 12 after material 11 has been placed inside. Any suitable seal can be used. Seal 12 should be capable of making a sufficiently water-tight closure so that liquid enters envelope 10 only by osmosis. Seal 12 can be formed from the same membrane material as envelope 10 or it can be made from another sealant. For example good results are obtained with Dow Corning Medical Adhesive A ® or by forming a plug of Dow Corning Silastic ® elastomer and allowing the elastomer to cure at room temperature.

Material 11 can be any solid or liquid material which is useful to establish osmotic pressure across the membrane which forms envelope 10 without degrading envelope 10. Materials which are useful as material 11 are salts such as sodium chloride, calcium chloride, magnesium chloride, magnesium sulphate, potassium sulphate, potassium chloride, sodium sulphate, sodium acetate, ammonium phosphate, ammonium sulphate, calcium lactate or magnesium succinate. Non-ionic substances such as sucrose, glucose, fructose, glycine, alanine, valine and vinyl pyrrolidone are also useful materials for establishing osmotic pressure. Hydrophillic (swellable or soluble) polymers such as poly-n-vinylpyrrolidone, carboxymethylcellulose and polyethylene glycols can be used as material 11 as can manitol, urea, blood by-products, proteins and dextran. Of course mixtures of any of the useful materials can also be used.

Sodium chloride is a preferred material because of the high osmotic pressure it provides. Material 11 can be present in any useful amount. The amount of material 11 used will vary primarily depending on the desired speed of expansion of envelope 10 and the desired final volume. For example, if very slow expansion is desired, the amount of material 11 will be chosen to result in a substantially isotonic fluid when completely in solution.

When a substantially constant rate of expansion is sought, an amount of material 11 is selected which will result in a saturated solution in envelope 10 even when it is completely expanded.

Figure 2:
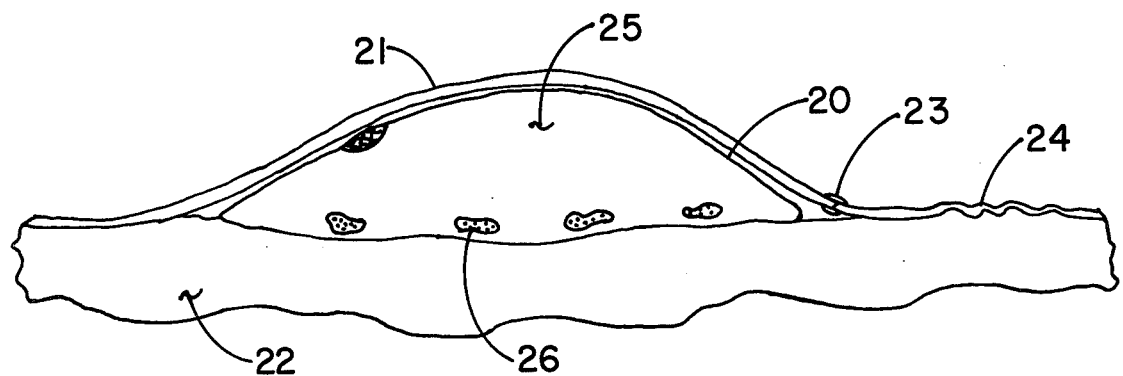
FIG. 2 shows schematically and in cross-section the device of the present invention after surgical implantation and expansion.

Referring more specifically to FIG. 2, there is shown an envelope 20 which has been surgically implanted under skin tissue 21. Envelope 20 is surgically implanted between skin tissue 21 and muscle tissue 22 when in a partially collapsed state (as shown in FIG. 1) through incision 23.

Envelope 20 is implanted in the vicinity of defect 24 which is sought to be repaired by subsequent plastic surgery.

Envelope 20 has expanded due to the passing of extracellular body fluid across the membrane which forms envelope 20. Skin 21 has expanded corresponding to the expansion of envelope 20. It is observed from experimental procedures that skin 21 can be extended without significant stretching or thinning.

Particles 26 are solid pieces of the material which provides the desired osmotic potential across the membrane wall of envelope 20, such as material 11 of FIG. 1. Particles 26 have not completely dissolved, indicating that solution 25 is a saturated solution. As discussed above, saturated solutions are often desirable when a steady rate of expansion is desired.

The degree of stretching of skin tissue 21 varies from case to case. In some instances, only limited stretching is required to supply expanded tissue for subsequent surgical procedures. In other situations, the greatest possible amount of tissue expansion is desired. Expansion of tissue up to at least about 170% its original surface area without undesirable thinning or disruption of vascular supply is observed in the practice of the present invention. This degree of expansion is observed in both skin tissue and mucous membrane. In cases where an even greater amount of skin is desired for correcting a defect, such as defect 24, skin expanding devices can be implanted at several sites around the defect.

The connective tissue and the direct vascular supply between muscle tissue 22 and skin tissue 21 is disrupted when envelope 20 is surgically implanted. However, skin tissue 21 is able to function adequately on the lateral vascular supply. Tissue 21 becomes trained to depend on the lateral vascular supply while envelope 20 is in place so that healthy tissue is available when envelope 20 is removed and skin tissue 21 is lapped to cover defect 24.

It is to be understood, however, that young, healthy tissue is preferred for expansion. The percentage of successful procedures tends to decrease in very old patients, as is true with previously known plastic surgery routines.

The type of defect 24 is not normally critical to the practice of the invention. The invention is found to be useful when defect 24 is, for example, a burn, a scar, bald scalp tissue, a tattoo or a cleft. The invention is also useful when expanded skin is required for subsequent insertion of a prosthesis, such as a mammary prosthesis.

In most applications, it is preferable to position the tissue expander over a bony prominence or a sheath of firm muscle so that the expansion will be predominently outward.

The invention will now be described by way of example.

EXAMPLE 1

An envelope was prepared of Dow Corning Silastic ® silicone rubber. The envelope has a wall thickness of about 0.006 inch (0.1524 mm) and is designed to have a length of about 4 cm.

Four ordinary salt (NaCl) tablets were placed in the envelope to provide a saturated solution. The envelope was sealed with Dow Corning Silastic ® silicone resin sealant and sterilized by autoclaving. Upon removal from the autoclave the envelope was observed to have substantially completely collapsed around the salt tablets.

The envelope was tested for leaks by submerging it for about 24 hours in a sterile water bath. After 24 hours the envelope was observed to have taken on some water by osmosis. (Excessive water intake would have indicated a pin-hole type leak).

A Guinea Pig was prepared to receive the skin expander device. The Guinea Pig was anesthesized and its back shaved. An antiseptic was applied to the shaved area. A small incision was made in the skin at one end of the shaved area, and the skin loosened from the subcutaneous tissue. The tissue expander was positioned under the skin, and the incision closed. The area of the skin covering the device was measured.

The Guinea Pig was observed for 4 weeks. During that time, the skin over the skin expander was seen to expand as the mass of the skin expander enlarged. At the end of 4 weeks, the expanded skin was measured and found to have expanded to about 1.7 times its original area.

The Guinea Pig was sacrificed and the entire area of the skin expander removed. The removed area was carefully dissected with special attention paid to the thickness of the expanded skin and to its vascular supply. The expanded skin was observed not to be undesirably thinned and to have an adequate vascular supply.

EXAMPLE 2

An envelope was prepared as in Example 1 and is immersed in a saline solution approximating extracellular body fluid (9 g/l.). The solution was maintained at a temperature of about 98.6° F. (37.0° C.) for 4 weeks.

The envelope was observed to expand to substantially the same degree as the envelope of Example 1.

EXAMPLE 3

Various envelopes were constructed as indicated in the table below, and were immersed in a warm saline bath (as in Example 2). The expansion characteristics of the envelopes are noted in the table.

designed to have an expanded shape substantially similar to that of a mammary prosthesis and to have an expanded volume of about 250 cc.

The envelope had a wall thickness of about 0.006 inch (0.1524 mm) and was filled with sufficient sodium chloride to result in an isotonic solution when fully expanded.

The envelope was sterilized and tested (as in Example 1) and was surgically implanted. The patient was carefully observed for a period of 6 weeks.

The tissue expander device was observed to cause the overlying skin tissue to expand slowly. At the end of the 6 week observation period the device was surgically removed and a mammary prosthesis was easily fitted under the expanded skin tissue.

EXAMPLE 5

A female patient is presented having a disfiguring scar on her back resulting from an automobile accident several years previous. The scar is long and fairly wide, extending down the patient's back from the shoulders to the top of the hip area.

Three tissue expander devices according to the present invention are prepared. The devices are designed to have a long narrow shape, and are made of Dow Corning Silastic ® silicone rubber having a wall thickness of about 0.003 inch (0.0762mm). The envelopes are filled with a sodium chloride solution in an amount sufficient to result in a saturated solution when completely expanded.

The envelopes are sterilized and tested (according to the procedure outlined in Example 1) and are surgically implanted under the patient's skin tissue along one side of the scar.

The tissue is carefully observed and is seen to expand at a relatively rapid rate. At the end of 4 weeks, it is determined that sufficient expansion of the skin tissue has been accomplished to provide tissue for repair of the scar.

| No. | Envelope Vol. | Envelope Material | Osmotic Material Type | Osmotic Material Amount | Observations Rate of Swell | Observations Envelope Strength | Usefulness for tissue expansion |
|---|---|---|---|---|---|---|---|
| ** 1 | 50 cc | Silastic* 0.001 in. (0.0254 mm) | NaCl | Sufficient for saturated solution | Rapid (6 ml/day) | Weak. Ruptured with rough handling | Questionable (weak) |
| 2 | " | Silastic* 0.002 in. (0.0508 mm) | " | " | Rapid (4.2 ml/day) | good | OK |
| 3 | " | Silastic* 0.006 in. (0.1524 mm) | " | " | Slower (1.8 ml/day) | good | OK |
| 4 | " | Silastic* 0.012 in. (0.3048 mm) | " | " | Slow (0.9 ml/day) | Excellent | Questionable (slow) |
| 5 | " | Silastic* 0.003 in. (0.0762 mm) | " | Sufficient for isotonic final solution | Varied. Rapid at first, but slowed greatly after first day | good | Questionable for most applications, Too slow |

*Dow Corning Silastic ® silicone rubber
**Calculated Example

EXAMPLE 4

A female patient was selected for receipt of a mammary prosthesis. The patient was observed to have one well developed breast and one breast which was not developed due to apparent surgical removal of the mammary gland tissue shortly after birth.

A tissue expander envelope was prepared from Dow Corning Silastic ® silicone rubber. The envelope was The skin expander devices are removed and the expanded tissue is used to repair the scar by ordinary plastic surgical procedure. The expanded skin is observed to be healthy and to have a sufficient vascular supply.

EXAMPLE 6

A newborn male with a unilateral cleft lip is presented. The patient is observed to have a skin and mucous membrane deficiency of about 40%. At 4 days of age an 18 cc envelope having a wall thickness of 0.006 inch (0.1524 mm) designed to provide a saturated salt (NaCl) solution is implanted subcutaneously in the lateral segment of the lip. At age 5 weeks, the device is removed and the expanded skin tissue and mucous membrane are utilized in a one-step closure of the lip.

The present invention has been disclosed in the above teachings, drawings and examples with sufficient clarity and conciseness to enable one skilled in the art to make and use the invention, to know the best mode for carrying out the invention and to distinguish it from other inventions and from what is old. Many variations and obvious adaptations of the inventions will readily come to mind, and these are intended to be contained within the scope of the invention as claimed below.

That which is claimed is:

1. A surgically implantable device for expanding skin tissue and mucous membrane, the device comprising a partially collapsed sealed flexible envelope formed substantially from a membrane which is permeable to extracellular body fluid and a material contained within the envelope which is selected to provide sufficient osmotic pressure across the membrane to draw extracellular fluid thereacross, causing the envelope to expand and resulting in corresponding expansion of tissue under which the device is implanted.

2. The device of claim 1 wherein the envelope is formed from a material selected from the group consisting of cellulose acetate, cellulose acetate butyrate, cellulose nitrate, crosslinked polyvinyl alcohol, polyurethanes, nylon 6, nylon 6.6, aromatic nylon, polyvinyl acetate, plasticized polyvinylacetate, polyvinyl butyrate, ethylene vinyl acetate copolymers, polyethylene, polypropylene, polyisobutylene, polyvinyl chloride, plasticized polyvinylchloride, natural rubber, silicone rubber and polybutadiene.

3. The device of claim 2 wherein the envelope is formed from a silicone rubber.

4. The device of claim 1 wherein the envelope has a wall thickness of from about 0.001 (0.0254 mm) to about 0.020 inch (0.5080 mm).

5. The device of claim 1 wherein the envelope has a potential volume of from about 10 ml. to about 300 cc.

6. The device of claim 1 wherein the material which provides osmotic potential across the membrane is selected from the group consisting of sodium chloride, calcium chloride, magnesium chloride, magnesium sulphate, potassium sulphate, sodium sulphite, potassium chloride, sodium acetate, ammonium phosphate, ammonium sulphate, sucrose, glucose, fructose, glycine, alanine, valine, vinyl pyrrolidone, poly-n-vinylpyrrolidone, calcium lactate, magnesium succinate, carboxymethylcellulose, polyethylene glycols, manitol, urea, proteins, blood by-products, dextran and mixtures thereof.

7. The device of claim 6 wherein the material which provides osmotic potential across the membrane is sodium chloride.

8. The device of claim 1 wherein the material which provides osmotic pressure across the membrane is present in an amount sufficient to achieve an isotonic solution in the envelope.

9. The device of claim 1 wherein the material which provides osmotic pressure across the membrane is present in an amount sufficient to provide osmotic pressure as long as the device is implanted.

10. A method for expanding skin tissue and mucous membrane in animals, the method comprising surgically implanting the device of claim 1 beneath the tisue and allowing the device to expand for a time sufficient to result in a corresponding tissue expansion.

11. The method of claim 10 including the subsequent step of surgically removing the device of claim 1.

12. The method of claim 11 including the additional subsequent step of using the expanded tissue in a surgical procedure.

13. The method of claim 12 wherein the device of claim 1 is surgically implanted sufficiently close to the site of the subsequent surgical procedure that the expanded tissue can be used in the subsequent procedure without totally interrupting the vascular supply to the expanded tissue.

14. The method of claim 11 including the additional subsequent step of using the expanded tissue to receive a prosthetic device.

15. The method of claim 14 wherein the prosthetic device is a mammary prosthesis.

* * * * *

UNITED STATES PATENT AND TRADEMARK OFFICE
CERTIFICATE OF CORRECTION

PATENT NO. : 4,157,085

DATED : June 5, 1979

INVENTOR(S) : ERIC D. AUSTAD

It is certified that error appears in the above-identified patent and that said Letters Patent are hereby corrected as shown below:

Column 2, line 22, "is" should read --in--.

Column 2, line 60, "osmatic" should read --osmotic--.

Column 8, line 26, "tisue" should read --tissue--.

Signed and Sealed this

Thirteenth Day of January 1981

[SEAL]

Attest:

SIDNEY A. DIAMOND

Attesting Officer   Commissioner of Patents and Trademarks